(12) United States Patent
Tabacco et al.

(10) Patent No.: US 7,190,457 B2
(45) Date of Patent: Mar. 13, 2007

(54) REAL-TIME BIOFILM MONITORING SYSTEM

(75) Inventors: Mary Elizabeth Tabacco, Brighton, MA (US); Marc W Mittelman, Canton, MA (US); J. Anthony Schanzie, Belmont, MA (US)

(73) Assignee: Echo Technologies, Inc., Alexandria, VA (US)

( * ) Notice: Subject to any disclaimer, the term of this patent is extended or adjusted under 35 U.S.C. 154(b) by 389 days.

(21) Appl. No.: 10/758,318

(22) Filed: Jan. 13, 2004

(65) Prior Publication Data

US 2005/0151971 A1    Jul. 14, 2005

(51) Int. Cl.
*G01N 21/25*    (2006.01)
(52) U.S. Cl. ..................... 356/417; 356/317
(58) Field of Classification Search ............. 356/417; 250/461.2
See application file for complete search history.

(56) References Cited

U.S. PATENT DOCUMENTS 5,372,936 A * 12/1994 Fraatz et al. ............. 436/172
6,755,074 B2 * 6/2004 Davison et al. ........... 356/318

* cited by examiner

*Primary Examiner*—Hwa (Andrew) Lee
*Assistant Examiner*—Kara Geisel
(74) *Attorney, Agent, or Firm*—Foley & Lardner LLP (57) ABSTRACT

Real time biofilm monitoring systems are provided. Said systems comprise single or multiple fiber-optic probes detecting wavelength-specific fluorescence from biomarkers of fouling organisms; a compact optoelectronic interface and data acquisition system interfaced with said probes, wherein said probe or probes are bifurcated and contain at least one excitation and at least one emission filter permitting the simultaneous resolution of multiple biomarkers.

30 Claims, 12 Drawing Sheets

Figure 1. Spectra and calibration curves for biomarkers

Figure 2. BLOCK DIAGRAM OF BIOFILM MONITORING SYSTEM
System Enclosure NEMA 4 (IP65)

Figure 3. Direct Fluorescence Detection of Biofilms

Figure 5. Optical signal as function of cell number

Figure 6. Calibration curves of the new BMS probe and test fixture using 3 bacterial solutions Figure 7. Correlation of the signal with cell count

- signal correlates with cell count
- sensor tracks dynamic changes in real time
- signal decreases when biocide applied or due to "sloughing off"

Figure 8. Multiple biomarkers allow discrimination from fluorescent interferents, e.g., common hydrocarbons

- Ar-HC's fluoresce at TRP $\lambda$
- no fluorescence at NADH $\lambda_{ex}$ Figure 9. Block diagram for multi-channel biofilm monitoring system for use in process fluids

Figure 10. New fiber-optic probe design

Fig. 11A

Fig. 11B 32 channel spectrograph for monitoring
signal from multiple biomarkers and potential interferents Figure 12. Concept using an excitation reference channel to correct for spectral interference from non-biological materials. Wavelengths are given as examples but can be any UV-VIS-NIR wavelengths.

REAL-TIME BIOFILM MONITORING SYSTEM

FIELD OF THE INVENTION

The invention relates to real time biofilm monitoring systems based on a single or on multiple fiber optic probes which detect wavelength-specific fluorescence from biomarkers of fouling organisms.

BACKGROUND OF THE INVENTION

Biological fouling is a significant problem in a wide variety of fluid handling systems. Traditional methods may not be effective at detecting a biofilm before irreversible damage is done.

In particular, both the vulnerability of water systems to bioterrorism and the increasing pressure on a limited fresh water resource require techniques for preventing infection and toxicity of water supplies. Because typhoid is a more acutely obvious problem than cancer or birth defects, society, at least in the U.S., has compromised potential long-term safety by emphasizing short-term protection from infection. Continuous pathogen suppression with biocides to control contamination in the waste discharges and drinking water distribution systems leads to exposure to low levels of established toxins/carcinogens from disinfection byproducts. Substitution of high-energy exposure (e.g. ultraviolet light or ozone) treatments at water treatment facilities for continuous chlorination can provide safe water that is free of disinfection byproducts, but can chemically modify drinking water refractory organic constituents, thereby promoting microbial regrowth in distribution systems if the water treatment or distribution system integrity allows refractory organics into the drinking water. This protection requires a much more effective water treatment.

It has been demonstrated that regrowth leads to biofilm formation, and that biofilms can both nurture pathogenic microbes and offer protection from biocides. The biofilms also concentrate drugs, hormones, and their mimics, as well as other pharmacologically active pollutants. These microbial biofilms in the distribution system can be major threats to freshwater reuse if water use for reuse is insufficiently treated to remove most organic carbon and trace nutrients.

Microbes in nature and in drinking water distribution systems are mostly concentrated in multispecies community biofilms rather than floating freely in fluids. A logical and cost-effective method for sampling water microbes is to incubate strategically placed coupons that stimulate colonization in hours to days rather than weeks. The coupons are subsequently recovered for analysis of the microbial biofilms from the waters, after which any required treatment is applied to the water. Reproducible generation of biofilms that can be infected and colonized by pathogens and concentrate some hydrophilic drug/hormone components has been demonstrated.

Several approaches to detection of biofilms have been demonstrated in the laboratory, which approaches are summarized in Table 1. Infrared absorption based on Attenuated Total Reflection (ATR) spectroscopy has been used to monitor the conditioning films that are an early harbinger of biofilm formation. ATR has also been studied for detection of suspended and biofilm bacteria. However, because of the limited depth of penetration of the evanescent wave into the surrounding medium, less than 1 micron of the film can be interrogated. Also, the resultant spectra are very complicated and convoluted because of the overlay of vibrational spectroscopic contributions from all the molecules in the interrogation region (Nivens et al., 1995). Many researchers have used fiber optic probes to transmit light to a solution or biofilm (Mittelman et al, 1993; Anders et al., 1993). Earlier research demonstrated that bacteria adhering to an unclad optical fiber can be detected in low numbers based on refractive index discontinuity (Tabacco, 1994). Fiber optics have also been used to measure backscattered light intensity in biofilms (Beynal et al., 2000). In this case the tapered fiber probes actually penetrate the biofilm. Backscattered near infrared light is correlated with local diffusivity as measured by a microelectrode, which in turn is correlated with the density of the biofilm. However, this technique does not specifically distinguish biological from nonbiological films that arise from mineral deposits.

TABLE 1

Technologies Applied to Biofilm Detection

| | |
|---|---|
| Evanescent wave—ATR | Limited depth of penetration; convoluted spectra |
| Fiber optic—refractive index | May not discriminate biological/non-bio |
| Mass—QCM | No discrimination, many interferents |
| Electrochemical—impedance, conductance | Indirect measurement/non-biological |
| Fluorescence—direct UV excitation | Excellent sensititvity; specific for bio-fouling |

Similarly, piezoelectric sensors such as quartz crystal microbalances monitor frequency shifts as mass accumulates on the sensor surface. They have been used to detect biofilms, but suffer from pressure and temperature interferences, and are responsive to any type of material (e.g., biological or abiological) landing on the surface (Nivens et al, 1993).

NASA has demonstrated a microscope based imaging system for monitoring the attachment and detachment of organisms in a biofilm upon application of biocide (Pierson et al., 2000).

Traditional methods have been ineffective at detecting a biofilm before fouling leads to disruptions in mechanical operations, losses in heat transfer efficiency, or materials deterioration. Alto, there are no real-time in situ models for monitoring biofilms that pose serious health risks to individuals in enclosed spaces, such as during long duration space missions. Continuous monitoring of surfaces for biofilm formation would represent a major advance in prevention, mitigation, and treatment efforts, and should greatly reduce personnel time and costs associated with adverse effects arising from biofilms.

SUMMARY OF THE INVENTION

It is an object of the present invention to overcome the aforesaid deficiencies in the prior art.

It is another object of the present invention to provide a technique for simultaneous detection of multiple biomarkers associated with biofilms.

It is a further object of the present invention to provide small optical detection and monitoring systems for detecting and monitoring biofilms.

The present invention is directed to an autonomous, stand-alone system that directly measures the bacteria responsible for biofilm formation. The biofilm monitor of the present invention can be used in-line, for a variety of process control applications in many industries.

The system combines a single or multiple fiber-optic probes that detect wavelength-specific fluorescence from biomarkers generic to all fouling organisms but which are not found in non-biological films. The sensor geometry is designed to be insensitive to bulk-phase bacteria and other interferents. The system requires no reagents or other consumables. Additional advantages of optical detection include: high sensitivity; relative insensitivity to interferent material; and the potential for multi-analyte/multi-wavelength analysis for greater measurement fidelity.

The present invention provides a new approach for real-time detection and quantitation of biofilms. This approach has been demonstrated for detection in situ, or external to a fluid handling system, and can detect biofilms on surfaces as diverse as glass, polycarbonate, metal or paint. The system consists of multiple optical probes interfaced with a compact optoelectronic interface and data acquisition system. Optical signals can be correlated in real time with biofilm growth and accretion. The system response is reversible and can monitor dynamic changes in the biofilm such as sloughing and can be used to monitor the efficacy of biocide application in real time. Data from the system are stored on compact flash cards, can be downloaded to a PDA or other computer, and can be telemetered via cell phone or satellite.

The present invention provides a fully integrated system for in situ or external monitoring of process and other fluids that detects, quantifies, analyzes, reports and stores data.

An ideal biofilm monitor should have the following characteristics:

a. In-line, in situ detection of bacteria on representative surfaces;

b. Ability to discriminate biological from abiological contamination;

c. High signal-to-noise ratio;

d. Ability to provide a reproducible quantitative correlation between optical signal and degree of fouling (i.e., some type of fouling index);

e. Immunity to interferents such as ionic strength, temperature, pressure, flow effects, and EMI (Electromagnetic Interference).

f. Data acquisition and processing electronics which are easy to use, self-contained, and which provide real-time analysis.

Many of these criteria can be met by optical techniques, more specifically, by fluorescence spectroscopy because of the many inherent fluorescent biomarkers associated with bacterial films. Sensitive real-time monitoring of biofilm growth, dynamics and removal can be achieved using direct fluorescence spectroscopy (Anders et al., 1993; Angel et al., 1993). There are several advantages to direct fluorescence detection, as summarized in Table 2. The system of the present invention, however, will allow both unequivocal discrimination of biological from abiological fouling, and will also provide valuable information about the biofilm metabolic status and dynamics, as well as potential for severe fouling and adverse health effects.

TABLE 2

DIRECT FLUORESCENCE DETECTION OF BIOFILMS

| Advantages | Potential Variables/Mitigation Factors |
|---|---|
| Generic to all fouling organisms | Photodegradation of the fluorophore or biofilm—modulate optical source & sample frequency |
| Relatively immune to non-biological interferences | Quenching of fluorescence—application specific, lab studies needed |
| Simplicity and availability of numerous COTS photonic components | Absorption of fluorescence—"front face" excitation/collection |
| Multi-wavelength analysis for enhanced discrimination | Source intensity changes due to presence of absorbers—exc. wavelength too short for most common interferents |

A number of biomarkers and relevant florescence wavelengths can be used for direct detection of biofilms. These are shown in Table 3.

TABLE 3

Biomarkers and relevant fluorescence wavelengths for direct detection of biofilms.

| Biomass Parameter | Excitation (nm) | Emission (nm) | Parameter |
|---|---|---|---|
| TRP, TYR, PHE | 260–280 | 348, 303, 282 | biomass |
| ATP | 272 | 380 | metabolic activity |
| NADH | 340 | 460 | reducing power |
| *Algae/chlorophyll b | 480 | 640 | biomass/cell energy |
| **bioluminescence | — | 490 | |
| ***non-biological (e.g., $CaCO_3$, $MgSO_4$) | | | fluid-borne deposits |

*possible presence in plant resource recovery or bioreactors
**may not be present in Life Support Systems
***could eventually monitor these parameters via fluor. or % transmission of excitation light to determine degree of scaling The method and apparatus of the present invention exploit biomarkers that are inherent to bacteria, so that no reagents or sample preparation are required. Because there are no competing reagents, multiple biomarkers can be detected with one probe.

Chemometrics analysis is used for advanced data processing from sensor arrays, or when looking at multiple components in one or more samples. Chemometrics includes analysis using principal component analysis, pattern recognition, neural networks, and fuzzy logic, for example.

In the present invention, chemometric processing is used to analyze the optical signal from multiple detection channels, each designed to detect a different biomarker, to confirm the presence of, and evaluate the status of, the biofilm. The chemometric process also aids in decision making to determine the efficacy of the biofilm removal efforts.

The method of the present invention develops application-specific "fouling parameter" algorithms for automated decision making. For example, a threshold is set that says if the biofilm monitor signal changes by "x" amount, an alarm or maintenance step would be initiated.

The apparatus of the present invention can be deployed in two configurations depending on the application. In the external configuration, the probe is isolated from the process fluid, and the probe monitors biofilms on representative surfaces. In the in-situ configuration, the probe is placed into process fluid. In this case the probe provides non-destructive detection with no contact of the biofilm. For this configuration, the probe is waterproof.

The apparatus of the present invention detects biofilms on many different substrates, including glass, plastic, metal, painted surfaces, etc. The apparatus provides direct correlation of the optical signal with cell count. The unique optical configuration of the system of the present invention distinguishes bulk or suspended bacteria from biofilm. When this system is bundled with the biosensor described in U.S. Pat. No. 6,485,962, assigned to Echo Technologies, Inc., the entire contents of which are hereby incorporated by reference, one can obtain an early measure of microbial contamination and incipient biofilm formation.

The system of the present invention detects biofilms from all common fouling organisms, including pigmented and non-pigmented bacteria, while being immune to other fluorescent markers used to signal biocide application. The optical configuration can be tailored to monitor very small or large surface areas.

Figure 12:
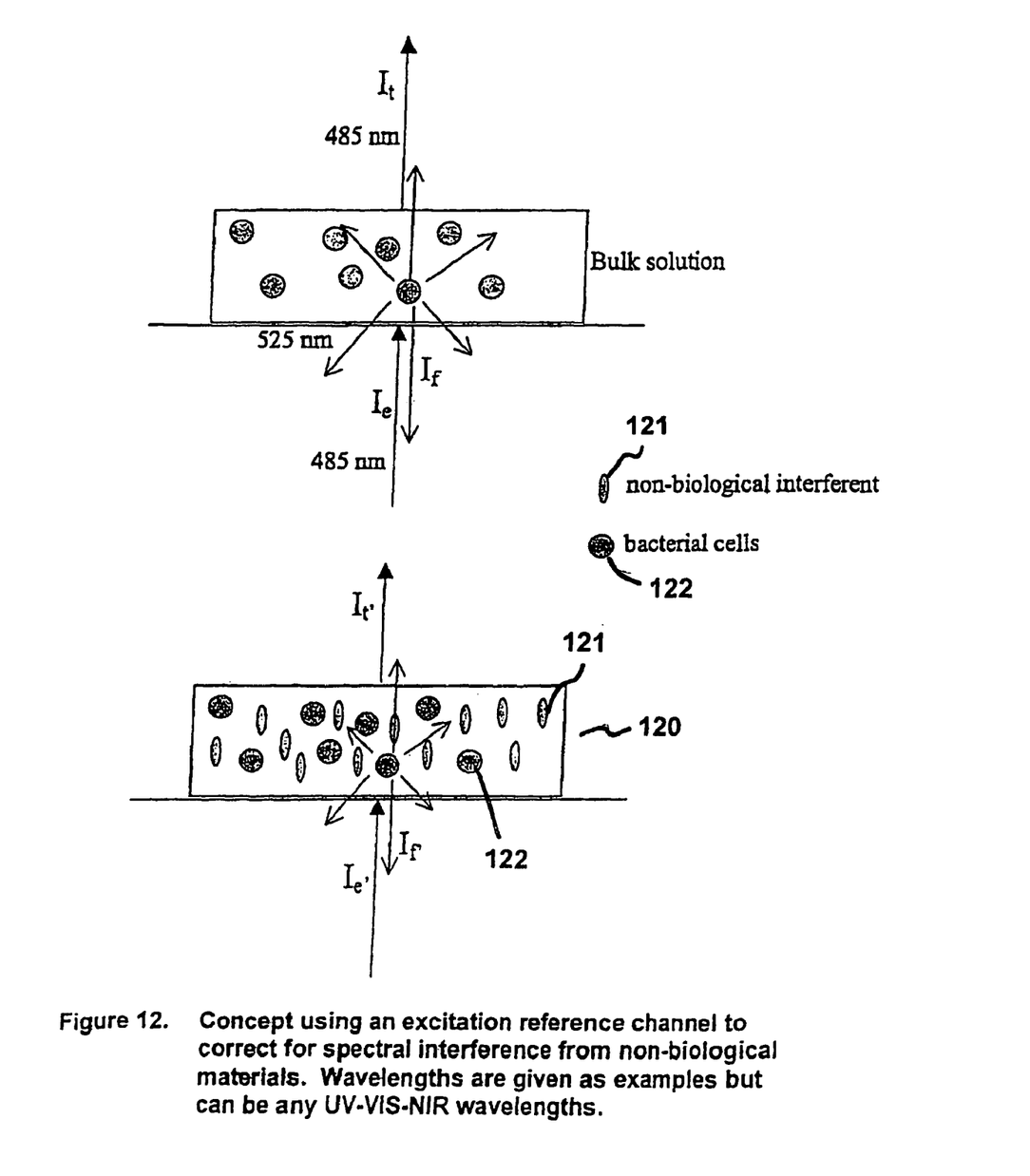
FIG. 12 illustrates the concept of using an excitation reference channel to correct for spectral interference from non-biological materials.

A reference channel is provided to monitor absorption and ratio of excitation and emission light to estimate turbidity of bulk solution, discriminate biofilms from potential organic interferents, such as fuel, oil, or humic matter. A reference channel tuned at the excitation wavelength may correct for optical interference and provide an estimate of turbidity, with a spectral ratiometric method as demonstrated in FIG. 12. $I_e$, $I_t$ and $I_f$ in FIG. 12 represent for the intensity of excitation, transmission and fluorescence, respectively. Wavelengths are given as examples but can be any UV-VIS-NIR wavelengths.

A change in the intensity of the optical excitation light provides an indication of turbidity. Other interferents can be potentially discriminated from biofilms based on the optical absorption properties, e.g., fuel, oils, humic matter. Recent work in the lab of the present inventors has demonstrated that interference due to the presence of non-biological interferents can be mitigated by measuring the ratio of fluorescence emission to optical excitation light.

DETAILED DESCRIPTION OF THE DRAWINGS

DETAILED DESCRIPTION OF THE INVENTION

The system of the present invention is generic to all fouling organisms while being relatively immune to non-biological interferents. Its simplicity and numerous COTS photonic components provide multiple biomarkers for multiwavelength analysis.

Figure 1:
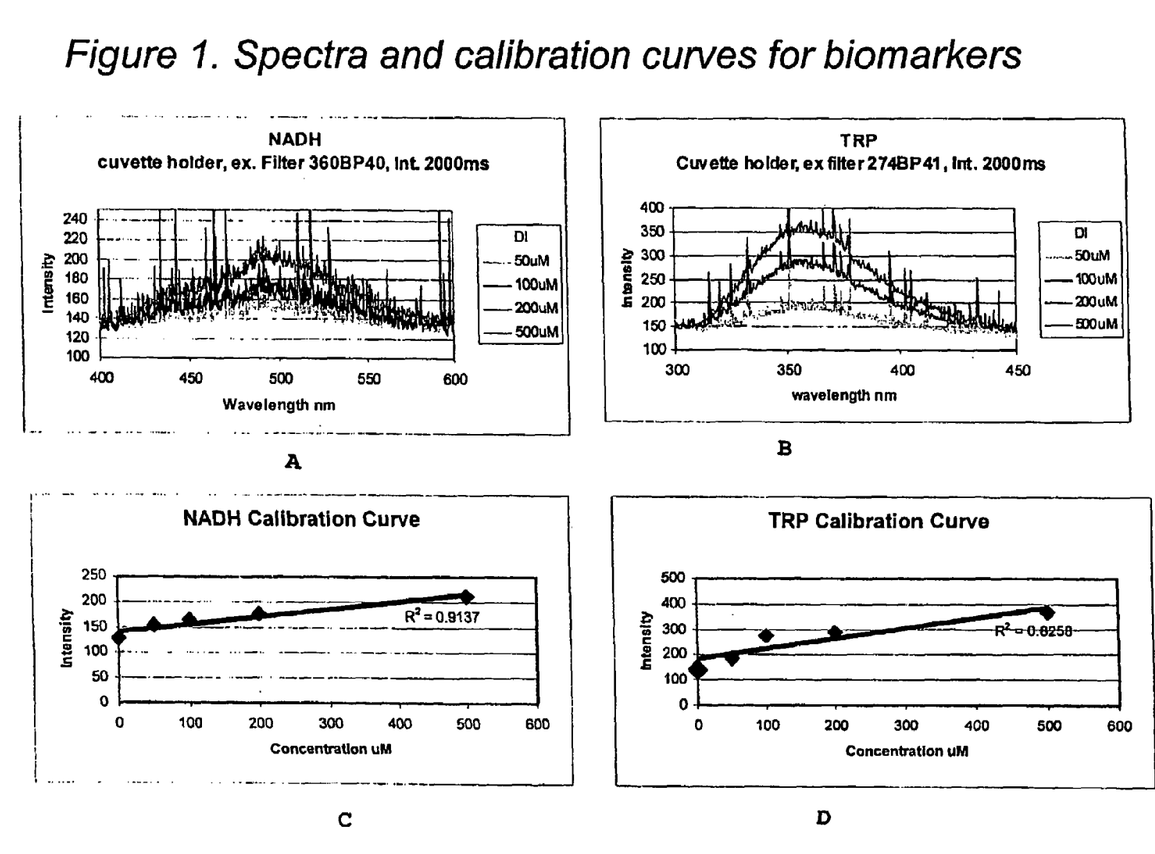
FIGS. 1a–d show spectra and calibration curves for biomarkers.
Figure 2:
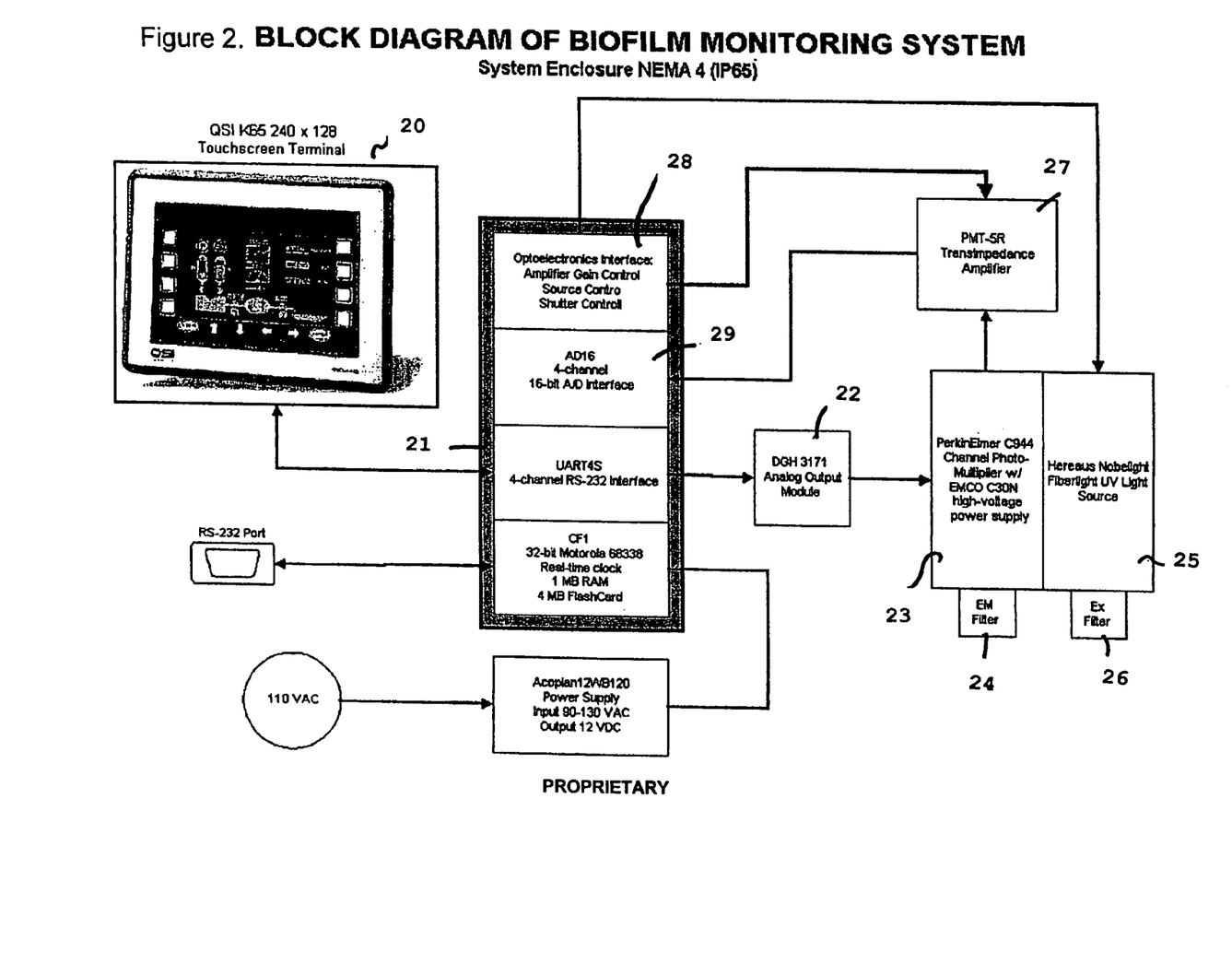
FIG. 2 is a block diagram of a biofilm monitoring system according to the present invention.

FIG. 2 is a block diagram of a biofilm monitoring system according to the present invention. The system is operated from a touch screen terminal 20 which is connected to a 4-channel RS-232 interface 21. This interface 21 is connected to an analog output module 22, connected to a C944 channel photomultiplier with a high-voltage power supply 23. The photomultiplier is provided with an emission filter. The photomultiplier is equipped with a fiber light UV light source 25, which has an excitation filter 26. The photomultiplier 23 is connected to a transimpedance amplifier 27 which is connected to both an optoelectronics interface amplifier 28 and a 4-channel 16-bit A/D interface 29.

Figure 3:
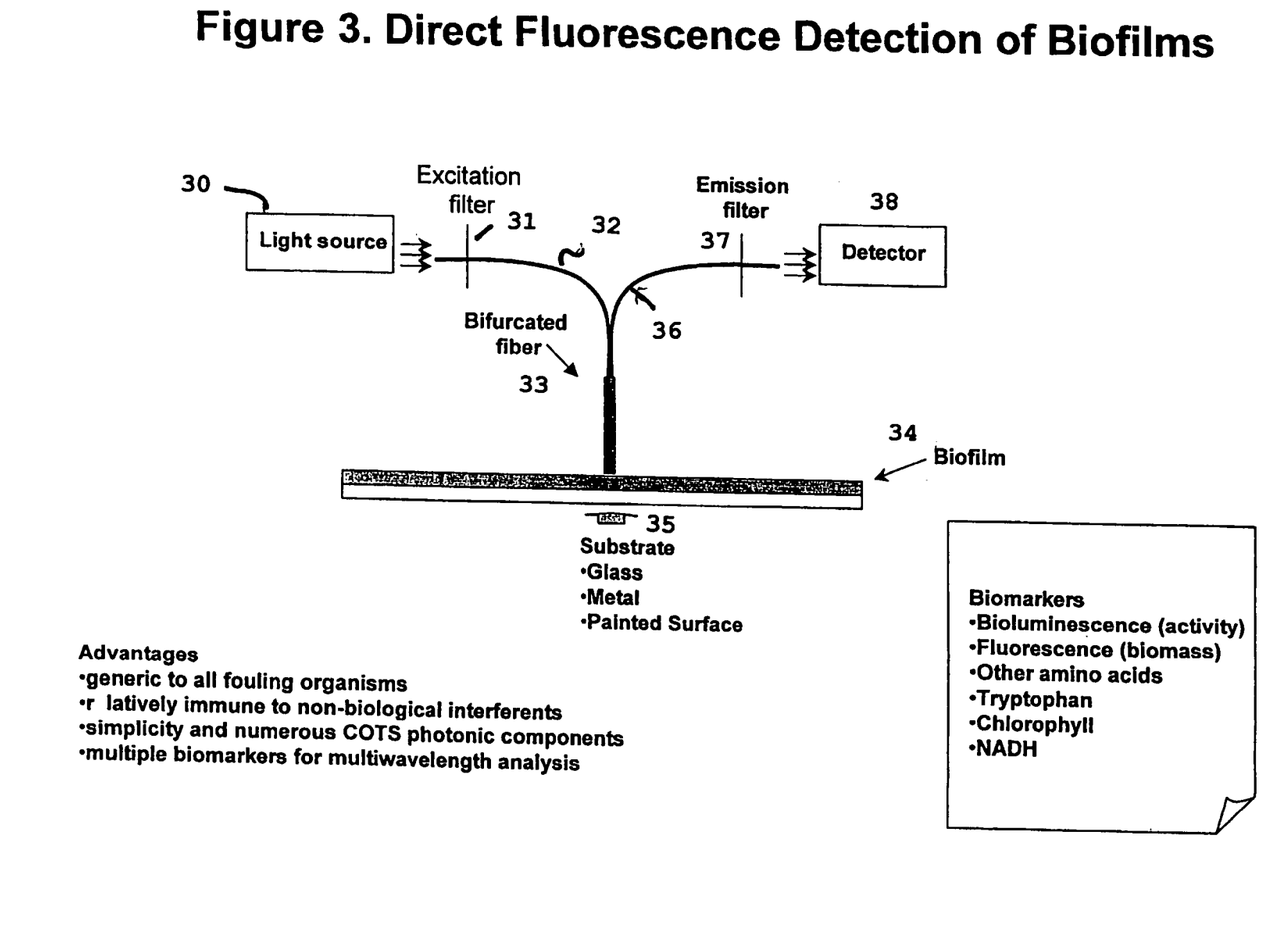
FIG. 3 illustrates direct fluorescence detection of biofilms.

FIG. 3 illustrates direct fluorescence detection of biofilms according to the present invention. A light source 30 sends light through an excitation filter 31 through an optical fiber 32. Optical fiber 32 becomes part of a bifurcated fiber 33, after which it contacts a biofilm 34 on a substrate 35. While the fiber optic probe is generally placed in a close proximity to the biofilm, biofilm can actually be allowed to form on the probe. The fiber optic probe can be placed directly into the process fluid, or behind an optical window on which the biofilm accumulates. The substrate can be any substrate, including glass, metal, plastic, painted surfaces, or the like. After the light from the bifurcated fiber 33 strikes the biofilm, one or more biomarkers, including fluorescence emission arising from bacteria and bacterial biomarkers from the biofilm from the light incident on the biofilm travels back up the bifurcated fiber 33 to a second optical fiber 36, through an emission filter 37, to a detector 37.

While this example shows one bifurcated fiber bundle, there can be a plurality of bifurcated fiber bundles. Each bundle has the appropriate transmission characteristics and is interfaced with appropriate excitation and emission filters, to selective detect at least one of the biomarkers listed in Table 3. The bifurcated fibers make it possible to transmit excitation light from the light source and collect and transmit the resulting fluorescence emission along the same optical fiber, i.e., the two "legs" of the same fiber.

The biomarkers can be bioluminescence, which indicates activity; fluorescence, which indicates biomass; other amino acids including tryptophan, tyrosine, phenylalanine, etc; chlorophyll; or NADH. This system is generic to all fouling organisms and is relatively immune to non-biological interferents. The components of the system are conventional off the shelf components, and multiple biomarkers can be detected for multiwavelength analysis.

Figure 4:
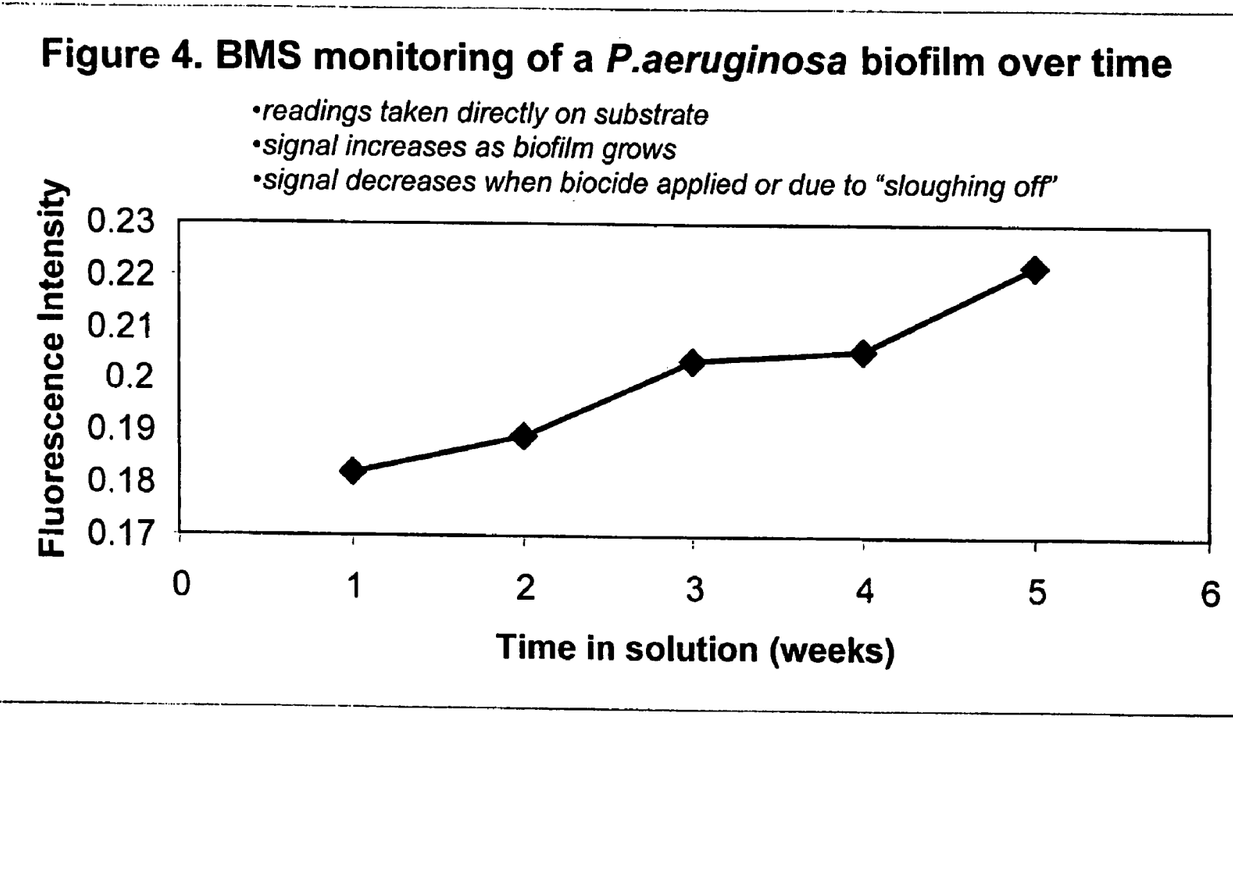
FIG. 4 illustrates BMS monitoring of a *P. aeruginosa* biofilm over time.
Figure 5:
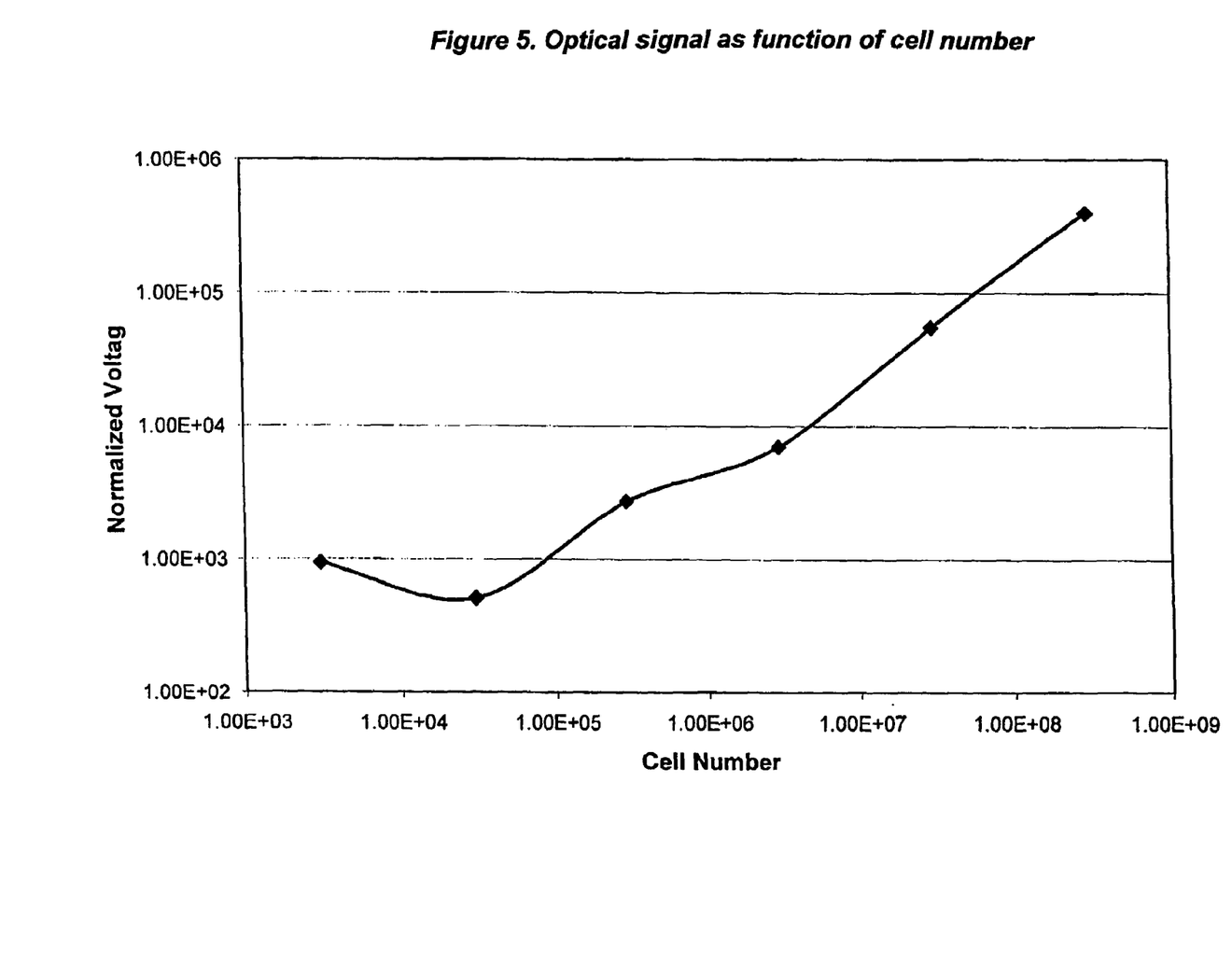
FIG. 5 shows that optical signal is a function of cell numbers.
Figure 6:
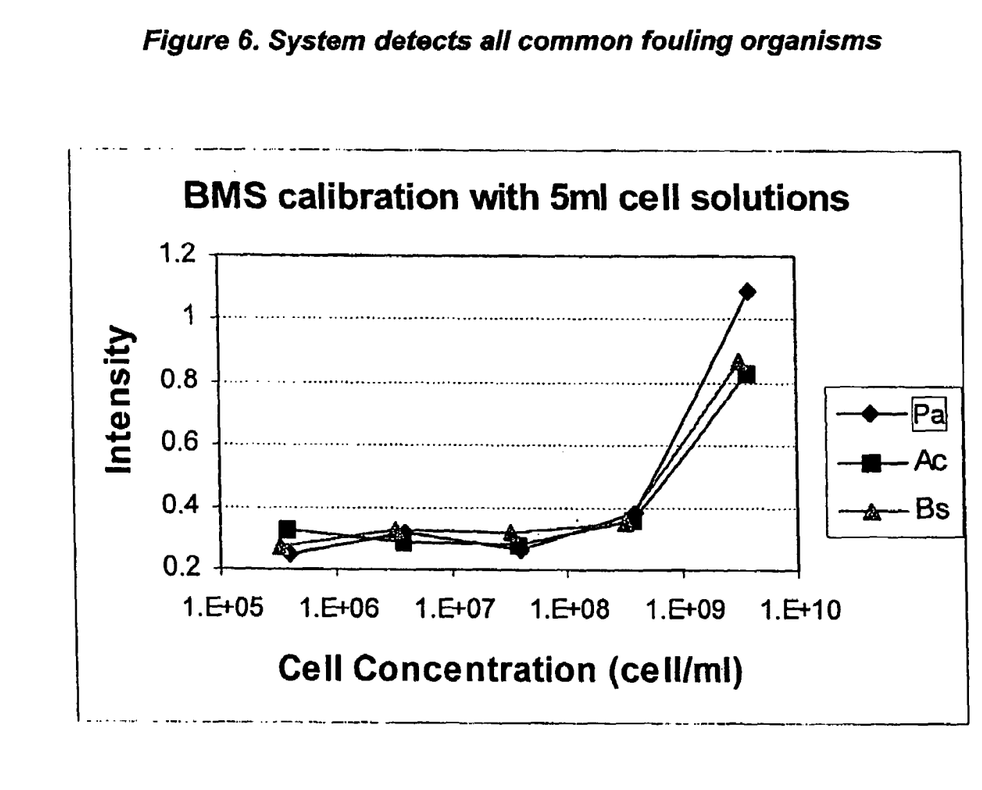
FIG. 6 shows that the system detects all common fouling organisms.

FIG. 4 illustrates monitoring of a *P. aeruginosa* biofilm over time, nearly six weeks. The readings were taken directly on the substrate on which the biofilm was growing, and the signal increases as the biofilm grows. The signal decreases when biocide is applied or if the biofilm sloughs off the substrate.

The advantage of the system of the present invention is that the system detects all common fouling organisms without interference from each organism detected.

Figure 7:
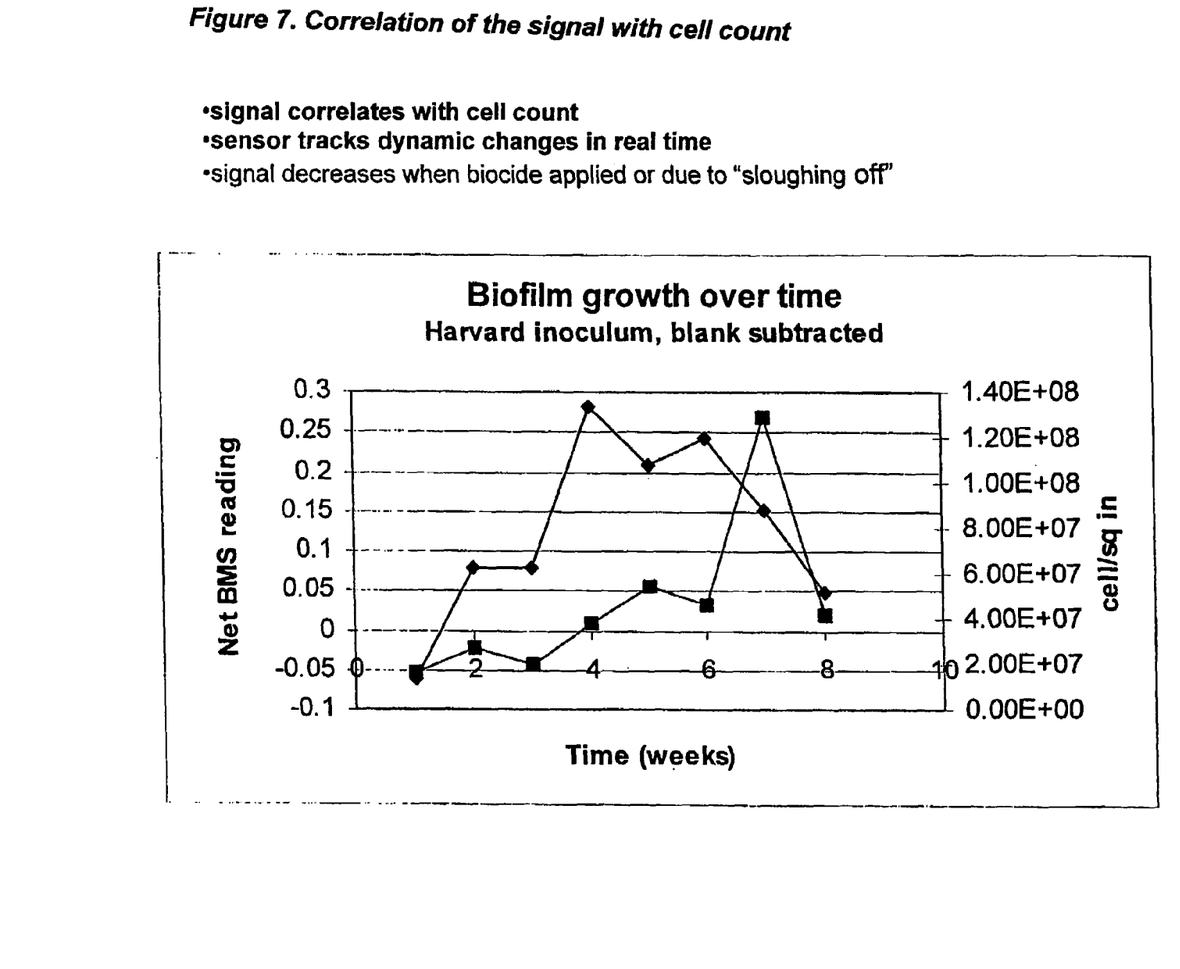
FIG. 7 shows correlation of signal with cell count.

FIG. 7 correlates signals with cell count for biofilm growth over time. In this case, the sensor tracked dynamic changes in real time. The signal decreased when biocide was applied or the biofilm sloughed off the substrate.

Figure 8:
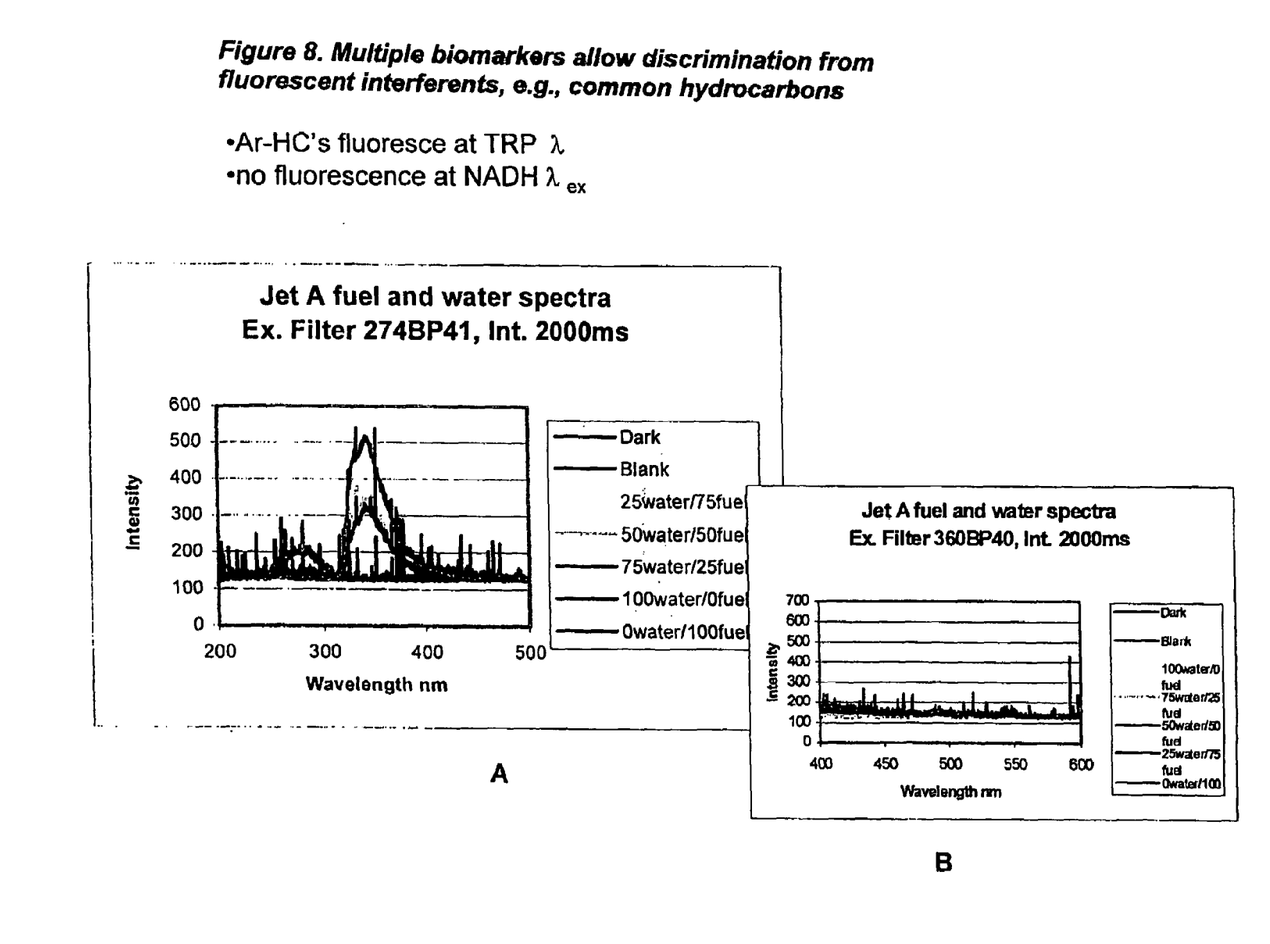
FIGS. 8A and 8B show that multiple biomarkers allow discrimination form fluorescent interferents.
Figure 9:
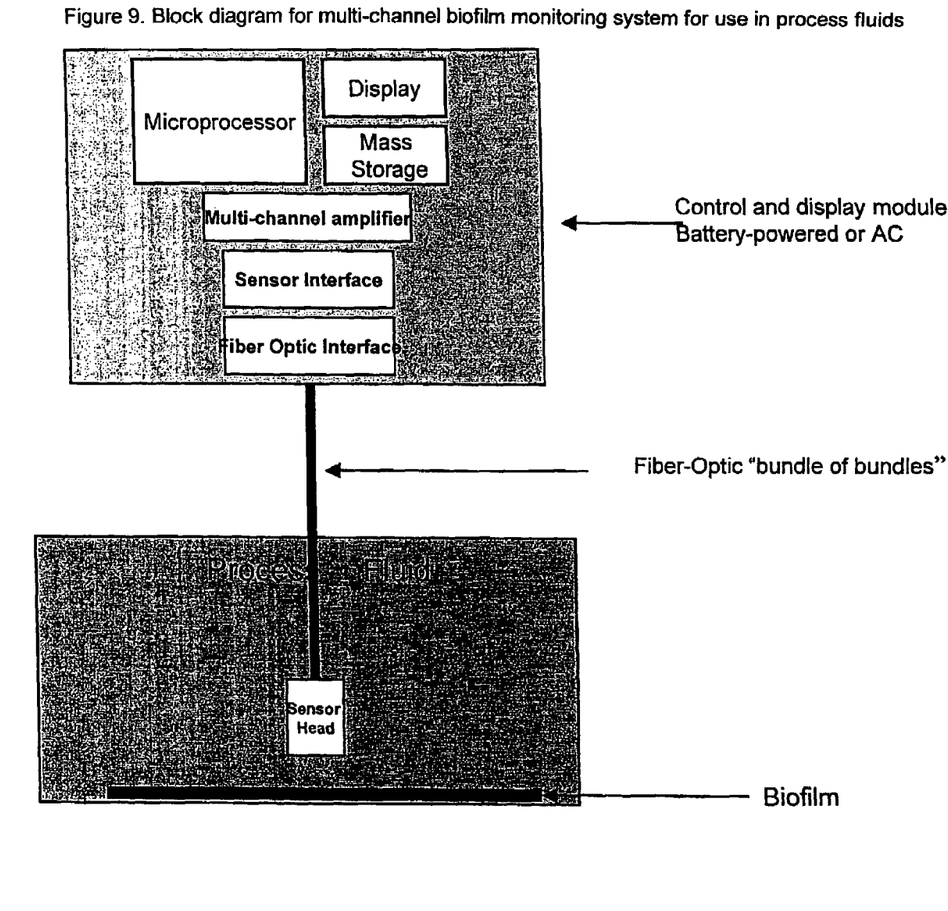
FIG. 9 is a block diagram for a multi-channel biofilm monitoring system for use in process fluids.
Figure 10:
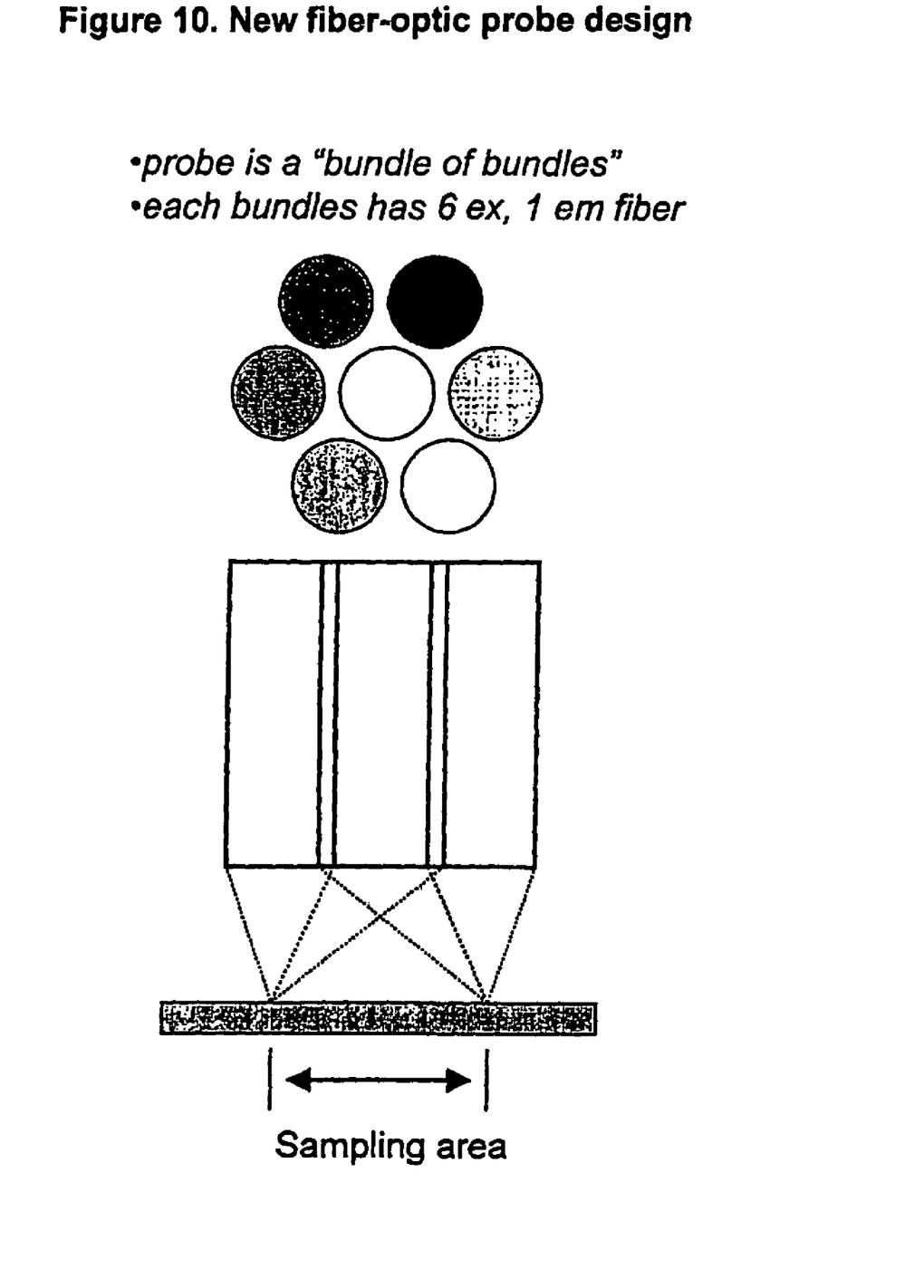
FIG. 10 shows a new design for a fiber optic probe.
Figure 11A:
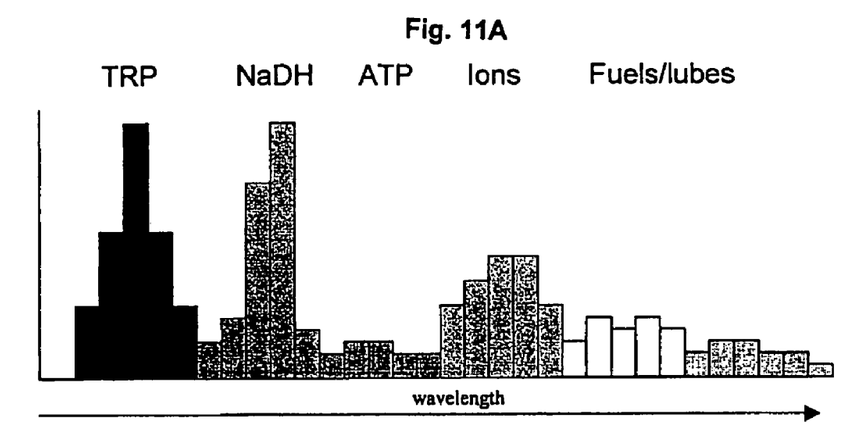
FIGS. 11A and 11B are 32 channel spectrographs for monitoring signals from multiple biomarkers and potential interferents.
Figure 11B:
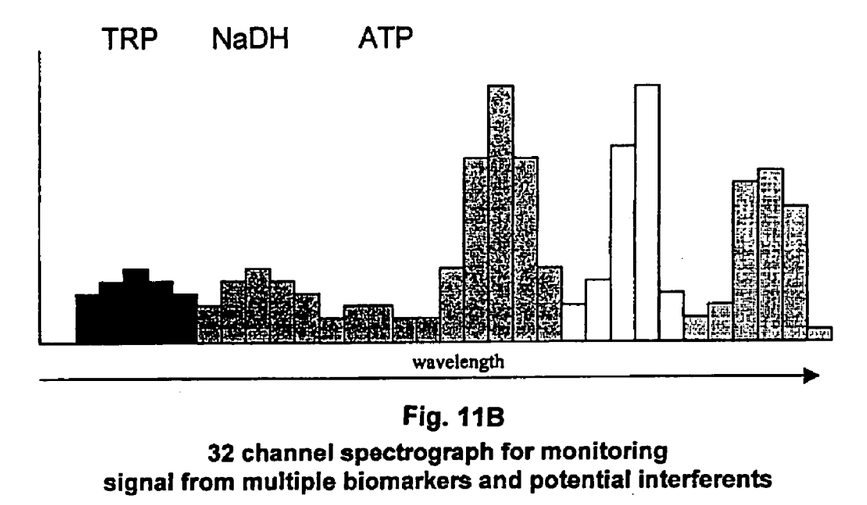

FIGS. 8A and B illustrate how multiple biomarkers make it possible to discriminate biofilms from fluorescent interferences such as common hydrocarbons. Aromatic hydrocarbons fluoresces at the wavelength for TRP (tryptophan) but to not fluoresce at the wavelength for detecting NADH.

The system of the present invention can be used to detect and/or monitor biofilms in process fluids, heat exchange systems, industrial processes, utilities plants, microelectronics fabrication system, pharmaceutical processing systems, food processing systems, and pulp and paper processing systems.

The system of the present invention makes it possible to detect and/or monitor biofilms to gauge how much and when a biocide should be applied, thus reducing costs associated with biocide application and with biofilm removal. The system also makes it possible to reduce costs associated with plant down time due to fouling.

The system of the present invention makes it possible to integrate the monitoring function with dosing with biocide. Particularly in the microelectronics and pharmaceutical industries, this can reduce costs and limit liability associated with the products.

The system of the present invention reduces long-term costs associated with biofilm detection and monitoring. The on-line and/or in situ detection eliminate down time in a plant.

The system provides for reagentless detection, with no requirement for sample preparation and/or user intervention. The system is fully autonomous; its operation is unattended, and there is no requirement for user expertise. The system is intrinsically safe from explosion or fire hazard.

The foregoing description of the specific embodiments will so fully reveal the general nature of the invention that others can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

REFERENCES

1. Nivens, D. E., Palmer, R. J., and Whitem D. C., "Continuous nondestructive monitoring of microbial biofilms: a review of analytical techniques," *J. Industrial Microbiology*, 15, pp. 263–276 (1995).
2. Mittelman, M., Packard, J., Arrage, A. A., Bean, S. L., Angell, P., and White, D. C., "Test systems for determining antifouling coating efficacy using on-line detection of bioluminescence and fluorescence in a laminar-flow environment," *J. of Micro. Methods*, 18, pp. 51–60 (1993).
3. Anders, K.-D., Wehnert, G., Thordsen, O., and Scheper, T., "Biotechnological applications of fiber-optic sensing: multiple uses of a fiber-optic fluorimeter," *Sensors and Actuators B*, 11, 395–403 (1993).
4. "Real-time Monitoring of Microbial Quality" Phase I & II SBIR, NASA Johnson Space Center (1993).
5. Beyenal, H., Lewandowski, Z., Yakymyshyn, C., Lemley, B. and Wehri, J., "Fiber-optic microsensors to measure backscattered light intensity in biofilms," *Applied Optics*, 39: 19, pp. 3408–3412 (2000).
6. Nivens, D. E., Chambers, J. Q., Anderson, T. R., and White, D. C., "Long-term, on-line monitoring of microbial biofilms using a quartz crystal microbalance," *Anal. Chem.*, 65, pp. 65–69 (1993).
7. Pierson, D. L. and Koenig, D. W. and Mishra, S. K., "Apparatus Measures Attachment or Detachment of Biofilm," NASA Tech Briefs, August 2000, p. 52.
8. Angell, P., Arrage, A. A., Mittelman, M., and White, D. C., "On line, non-destructive biomass determination of bacterial biofilms by fluorometry," *J. Micro. Methods*, 18 pp. 317–327 (1993).
9. Tabacco, M. B., Downing, J., and DiGiuseppe, T. G., "Development of Real Time Optical Sensors for Maintaining Microbial Quality," GEO-CENTERS, Inc. Final Report, GC-TR94-2707, July, 1994.

What is claimed is:

1. A real-time biofilm monitoring system comprising:
at least one fiber-optic probe that detects fluorescence of an inherent biomarker of a fouling organism, and
a compact optoelectronic interface and data acquisition system interfaced with said probe, wherein said probe is bifurcated and contains at least one excitation and at least one emission filter capable of resolution of multiple emission wavelengths that can be correlated to the presence or absence of an inherent biomarker.

2. The real-time biofilm monitoring system of claim 1, comprising multiple fiber-optic probes.

3. The real-time biofilm monitoring system according to claim 1, further comprising an excitation reference channel to correct for spectral interference from non-biological materials.

4. The real-time bioflim monitoring system according to claim 2, further comprising an excitation reference channel to correct for spectral interference from non-biological materials.

5. The real-time biofilm monitoring system of claim 1, wherein the system detects fluorescence in situ, in-line, or external to a sample.

6. The real-time biofilm monitoring system of claim 1, wherein the system does not include additional reagents or consumables.

7. The real-time biofilm monitoring system of claim 1, wherein the biomarker is selected from the group consisting of an amino acid, ATP, NADH, chlorophyll, and bioluminescence.

8. The real-time biofilm monitoring system of claim 7, wherein the amino acid is selected from the group consisting of Trp, Tyr, and Phe.

9. The real-time biofilm monitoring system of claim 7, further comprising detecting % transmission of excitation light.

10. The real-time biofilm monitoring system of claim 8, wherein a change in the % transmission of excitation light can be correlated to scaling due to non-biological materials selected from the group consisting of $CaCO_3$ and $MgSO_4$.

11. The real-time biofilm monitoring system of claim 1, wherein the system is capable of simultaneous resolution of multiple inherent biomarkers.

12. The real-time biofilm monitoring system of claim 1, wherein the system detects fluorescence of at least one inherent biomarker using multiple excitation wavelengths or multiple emission wavelengths.

13. The real-time biofilm monitoring system of claim 1, wherein the probe performs direct fluorescence detection of a inherent biomarker.

14. The real-time biofilm monitoring system of claim 1, wherein the system measures sloughing of a biofilm from a substrate.

15. A method for detecting a fouling organism comprising detecting fluorescence of an inherent biomarker comprising:
   a. introducing excitation light into a first side of a bifurcated optical fiber bundle directed at a sample;
   b. obtaining an emission arising from a substrate through a second side of a bifurcated optical fiber bundle; and
   c. detecting the emission from the substrate and correlating the emission to the presence or absence of a fouling organism.

16. The method according to claim 15, wherein the fouling organism is *P. Aeruginosa*.

17. The method according to claim 15, wherein the sample is selected from the group consisting of a process fluid, a heat exchange system, a utility plant, a microelectronics fabrication system, a food processing system, a fluid handling system, and pulp and paper processing system.

18. The method according to claim 15, wherein the sample comprises a substrate selected from the group consisting of glass, polycarbonate, metal, and paint.

19. The method according to claim 16, wherein the sample comprises a substrate selected from the group consisting of glass, polycarbonate, metal, and paint.

20. The method of claim 15, wherein the emission from a bulk phase bacteria is distinguishable from emission from the biofilm.

21. The method of claim 15, wherein the method is performed in situ, in-line, or external to a sample.

22. The method of claim 15, wherein the biomarker is selected from the group consisting of an amino acid, ATP, NADH chlorophyll, and bioluminescence.

23. The method of claim 22, wherein the amino acid is selected from the group consisting of Trp, Tyr, and Phe.

24. The method of claim 15, further comprising detecting % transmission of excitation light.

25. The method of claim 15, wherein the system is capable of simultaneous resolution of multiple inherent biomarkers.

26. The method of claim 15, wherein multiple excitation wavelengths are introduced or multiple emission wavelengths are detected.

27. The method of claim 15, wherein the method comprises direct fluorescence detection of a inherent biomarker.

28. The method of claim 15, further comprising distinguishing a bulk phase bacteria from the biofilm.

29. A method for detecting a plurality of fouling organisms comprising detecting fluorescence of an inherent biomarker comprising:
   a. introducing excitation light into a plurality of first sides of a plurality of bifurcated optical fiber bundles directed at a sample, wherein the excitation light can be the same or different for each first side of the bifurcated optical fiber bundles;
   b. obtaining emissions arising from a substrate through second sides of a plurality of bifurcated optical fiber bundles; and
   c. detecting the emission from the substrate and correlating this emission to the presence or absence of fouling organisms.

30. The method according to claim 29, wherein the sample is selected from the group consisting of a process fluid, a heat exchange system, a utility plant, a microelectronics fabrication system, a food processing system, a fluid handling system, and pulp and paper processing system.

* * * * *